United States Patent
Cahalane et al.

(10) Patent No.: US 10,925,610 B2
(45) Date of Patent: Feb. 23, 2021

(54) DEVICES FOR TREATING PARAVALVULAR LEAKAGE AND METHODS USE THEREOF

(71) Applicant: Edwards Lifesciences Corporation, Irvine, CA (US)

(72) Inventors: Steven Cahalane, Pelham, NH (US); Jason Robinson, Windham, NH (US)

(73) Assignee: Edwards Lifesciences Corporation, Irvine, CA (US)

( * ) Notice: Subject to any disclaimer, the term of this patent is extended or adjusted under 35 U.S.C. 154(b) by 108 days.

(21) Appl. No.: 16/249,470

(22) Filed: Jan. 16, 2019

(65) Prior Publication Data
US 2019/0254677 A1    Aug. 22, 2019

Related U.S. Application Data

(63) Continuation of application No. 15/061,549, filed on Mar. 4, 2016, now abandoned.
(Continued)

(51) Int. Cl.
*A61B 17/12* (2006.01)
*A61B 17/00* (2006.01)
(Continued)

(52) U.S. Cl.
CPC .... *A61B 17/12022* (2013.01); *A61B 17/0057* (2013.01); *A61B 2017/00004* (2013.01);
(Continued)

(58) Field of Classification Search
CPC .......... A61F 2/246; A61F 2/24; A61F 2/2409; A61F 2/2433; A61F 2/2418;
(Continued)

(56) References Cited

U.S. PATENT DOCUMENTS 3,604,488 A    9/1971   Wishart et al.
3,656,185 A    4/1972   Carpentier
(Continued)

FOREIGN PATENT DOCUMENTS

EP    1034753 A1    9/2000
EP    3531975 A1    9/2019
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Katrina M Stransky
(74) *Attorney, Agent, or Firm* — Thomas C. Richardson

(57) ABSTRACT

An aspect of the present teachings includes a method of percutaneously treating a paravalvular leakage. In a preferred embodiment, the method includes providing an anchor having an elongate anchor member and a tensioning member, positioning the anchor through a paravalvular leakage, deploying the anchor wherein at least a part of the distal portion of the elongate anchor member is on one side of the paravalvular leakage, and applying tension to the tensioning member so that at least a part of the distal portion of the elongate anchor member transitions from the elongate configuration to the shortened configuration. Another aspect of the present teachings includes a device that can be used in a method of percutaneously treating a paravalvular leakage.

22 Claims, 16 Drawing Sheets

Related U.S. Application Data

(60) Provisional application No. 62/128,997, filed on Mar. 5, 2015.

(51) Int. Cl.
   *A61B 17/04* (2006.01)
   *A61F 2/24* (2006.01)

(52) U.S. Cl.
   CPC .............. *A61B 2017/00575* (2013.01); *A61B 2017/00606* (2013.01); *A61B 2017/00619* (2013.01); *A61B 2017/0406* (2013.01); *A61B 2017/0419* (2013.01); *A61F 2/24* (2013.01); *A61F 2220/0075* (2013.01); *A61F 2250/0069* (2013.01)

(58) Field of Classification Search
   CPC ...... A61B 17/0057; A61B 2017/00004; A61B 2017/00575; A61B 2017/00606; A61B 2017/00619; A61B 2017/0419; A61B 17/0401; A61B 2017/0459
   See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |

(56) References Cited

U.S. PATENT DOCUMENTS

| | | |
|---|---|---|
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alterness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashnski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |

(56) References Cited

U.S. PATENT DOCUMENTS

| | | |
|---|---|---|
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Aikhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,645,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,259,218 B2 | 2/2016 | Robinson |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,730,793 B2 | 6/2017 | Reich et al. |
| 9,693,865 B2 | 7/2017 | Gilmore et al. |
| 9,724,084 B2 | 8/2017 | Groothuis et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |

(56) References Cited

U.S. PATENT DOCUMENTS

| | | |
|---|---|---|
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0010857 A1* | 1/2007 | Sugimoto ........ A61B 17/00234 606/232 |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Depen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |

(56) References Cited

U.S. PATENT DOCUMENTS

| | | |
|---|---|---|
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168645 A1 | 7/2010 | Wrigrit |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |

(56) References Cited

U.S. PATENT DOCUMENTS

| | | |
|---|---|---|
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0190226 A1* | 7/2015 | Johnson ............... A61F 2/24 623/2.38 |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al. "Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure," The Thoracic and cardiovascular surgeon 47.01 (1999): 51-52.

Dang NC et al, "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept," Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

(56) References Cited

OTHER PUBLICATIONS

Odell JA et al., "Early Results o4yf a Simplified Method of Mitral Valve Annuloplasty," Circulation 92:150-154 (1995).
O'Reilly S et al.; "Heart valve surgery pushes the envelope," Medtech Insight 8(3): 73, 99-108 (2006).
Park, Sang C. et al. "A percutaneously adjustable device for banding of the pulmonary trunk," International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T,I., 1978, An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

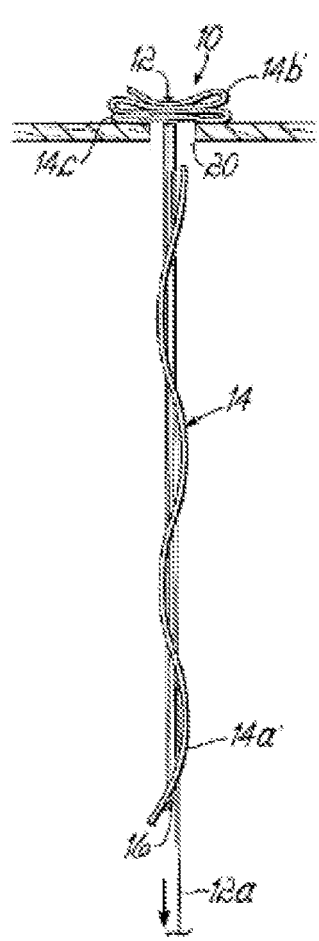 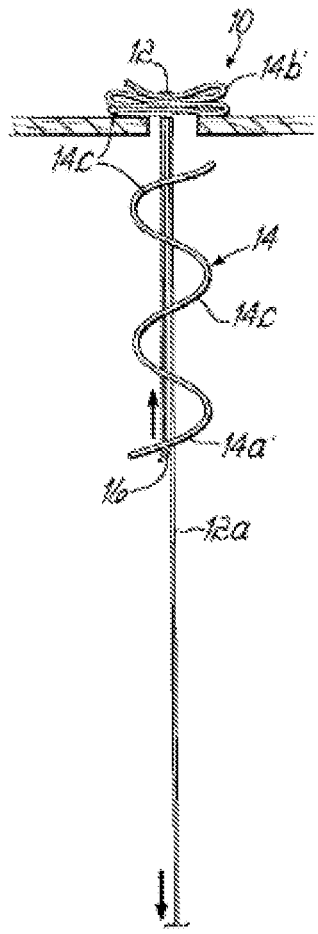 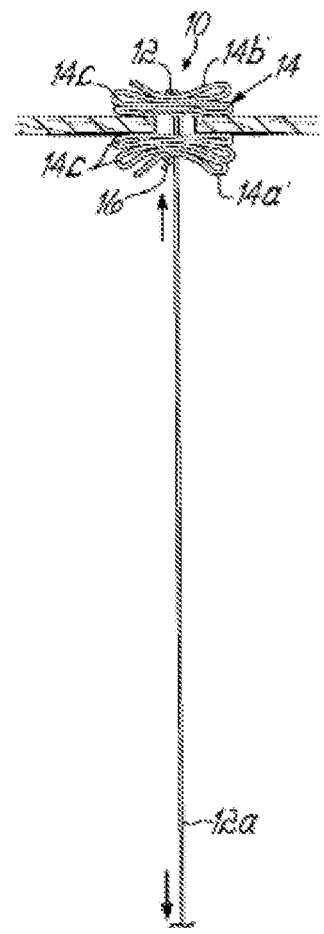
FIG. 3I     FIG. 3J     FIG. 3K
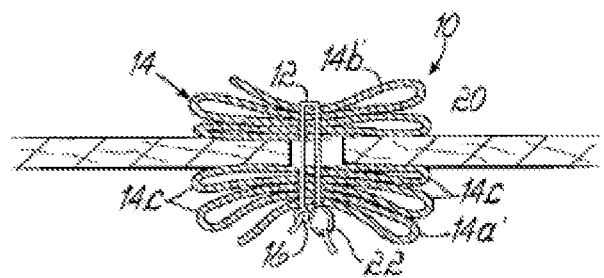
FIG. 3L

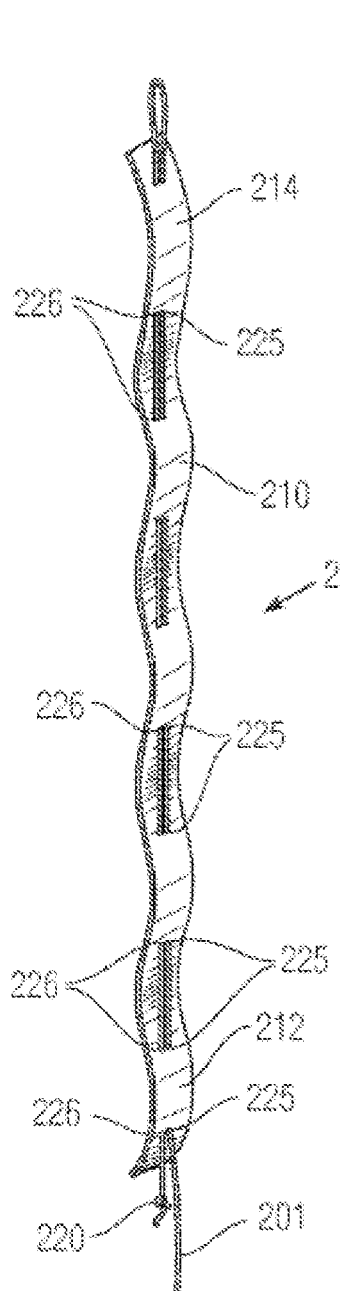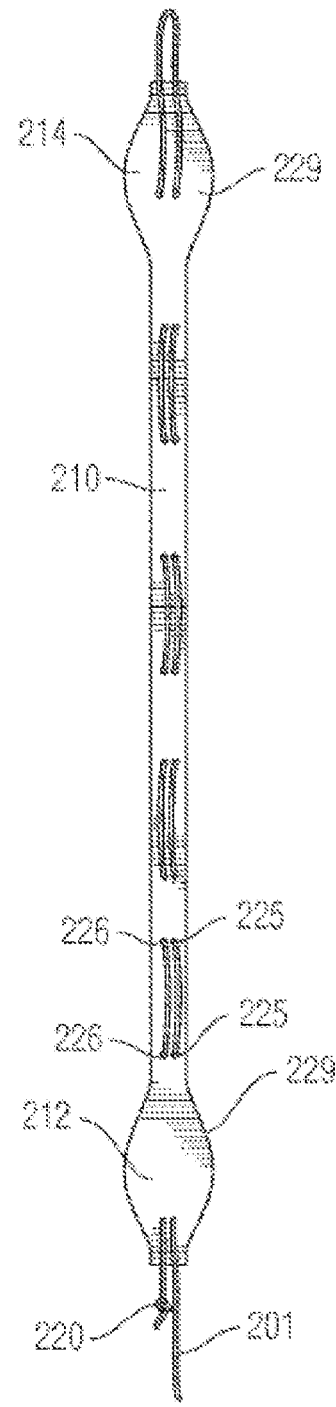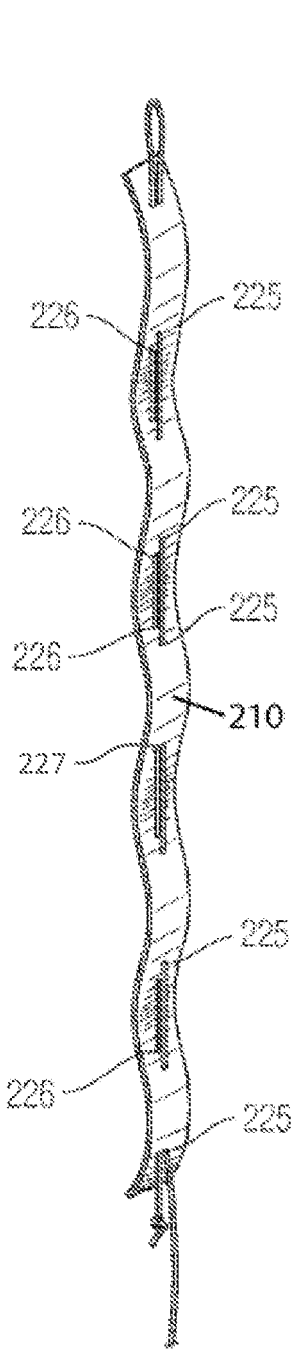
FIG. 7A
FIG. 7B
FIG. 7C

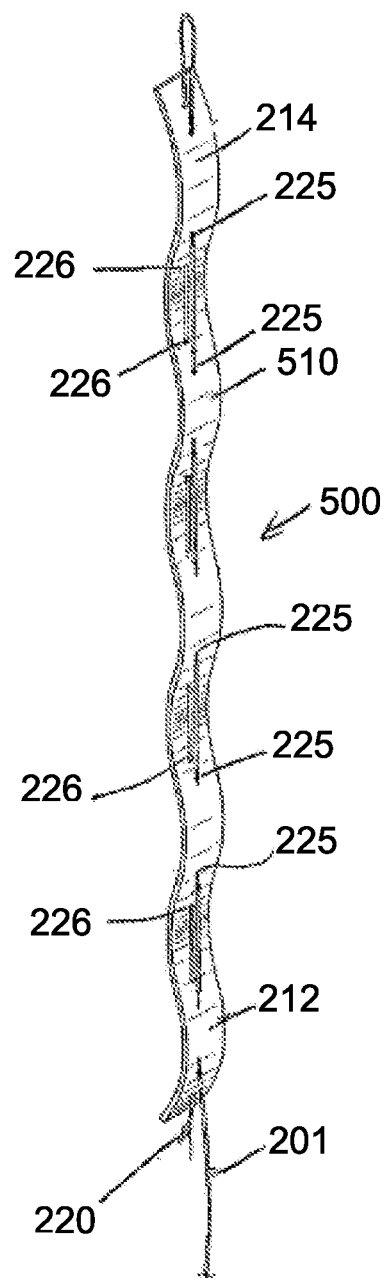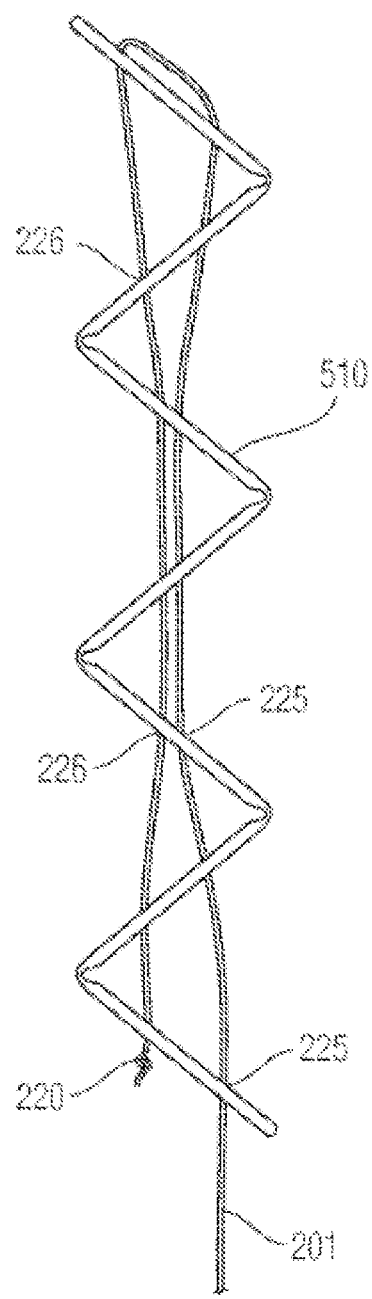
FIG. 10A
FIG. 10B

DEVICES FOR TREATING PARAVALVULAR LEAKAGE AND METHODS USE THEREOF

CROSS-REFERENCE TO RELATED APPLICATION

This application is a continuation of U.S. Non-Provisional patent application Ser. No. 15/061,549, filed Mar. 4, 2016, which is based on and claims priority to U.S. Provisional Patent Application No. 62/128,997, filed Mar. 5, 2015, all of which are incorporated by reference, as if expressly set forth in their respective entireties herein.

BACKGROUND

Paravalvular leakage is a complication associated with the implantation of a prosthetic valve. It may occur both in traditional surgical or minimally invasive transcatheter approaches. FIG. 1 illustrates an artificial valve 1600 that may include, for example, a multi-leaflet structure 1602 and that may be implemented in an appropriate manner as will be appreciated by those of ordinary skill in the art. Additionally, a small opening or space 1604 between the heart 1606 and the valve 1600 is shown as may occur in some instances of valve replacement. This opening or space 1604 results in undesired leaking during pumping of the heart and is termed a valvular or paravalvular leak.

Accordingly, devices and methods are needed for correcting paravalvular leakage after implantation of a stented prosthetic valve.

BRIEF SUMMARY OF THE INVENTION

One aspect of the present teachings includes an anchor for treating a paravalvular leakage. In various embodiments, the anchor includes at least one elongate anchor member. In some embodiments, the anchor includes one elongate anchor member. In some embodiments, the anchor includes two elongate anchor members. In yet other embodiments, the anchor includes three or more elongate anchor members. In certain embodiments, the two, three, or more elongate anchor members are made of a same material. In certain other embodiments, the two, three, or more elongate anchor members are made of different materials.

In some embodiments, the anchor has an elongate configuration where the elongate anchor member is relaxed and extended. In some embodiments, the anchor has a shortened configuration when the elongate anchor member(s) is folded or otherwise shortened. In certain embodiments, the anchor is in its shortened configuration when deployed and/or secured.

According to various embodiments of the present teachings, the elongate anchor member is made of a flexible material. In some embodiments, the flexible material is a surgical grade fabric. The elongate anchor member may also take various forms such as woven or nonwoven fabrics, polymers, metals, other suitable materials, or combinations thereof. For example, the surgical grade fabric used in various embodiments of the present teachings can be constructed from a polyester, such as Dacron®, RTM, PTFE, UHMPE, HDPE, polypropylene, polysulfone, or other biocompatible plastic.

In various embodiments, the elongate anchor member causes a tissue response, for example, tissue growth. In some embodiments, the surface finish of the anchor member is textured to induce tissue response and tissue in-growth for improved stabilization. In other embodiments, the anchor member comprises porous materials to promote tissue ingrowth.

In various embodiments, one or more of the edges and/or other portions of the anchor member are modified, for example, to prevent from fraying. In some embodiments, one or more of the edges or other portions of the anchor member are coated with a material that locks the fibers in place. Other methods can also be used to lock the fibers at one or more edges of the anchor member in place.

In various embodiments, the anchor includes at least one tensioning member. In some embodiments, the tensioning member causes both ends of the elongate anchor member to move towards each other. This motion can create a shortened distal portion and/or a shortened proximal portion. In certain embodiments, doing so secures the paravalvular leakage between the distal and the proximal portions of the elongate anchor member.

In embodiments where an anchor of the present teachings includes two elongate anchor members, the tensioning member causes at least one of the two elongate anchor members to move towards the other elongate anchor member. In certain embodiments, the tensioning member causes both of the elongate anchor members to move towards each other. In embodiments where an anchor of the present teachings includes three or more elongate anchor members, the tensioning member causes at least one of the three or more elongate anchor members to move towards another elongate anchor member. In certain embodiments, the tensioning member causes all of the three or more elongate anchor members to move towards one another. This motion can create shorten elongate anchor members. In certain other embodiments, doing so secures the paravalvular leakage between two of the elongate anchor members.

According to various embodiments of the present teachings, the tensioning member is in the form of a suture, as defined herein. It will be appreciated that the tensioning member may take forms other than a suture, such as any other small-diameter members having a suitable tensile strength for the intended anchoring use.

In various embodiments, one or both of the tensioning member and the elongate anchor member are made of a resorbable polymer. In some embodiments, such a resorbable polymer is polyactic acid, polyglycolic acid, polycaprolactone, or a combination thereof. Other resorbable polymers that are known to those skilled in the art can also be used without undue experimentation and thus are within the scope of the present teachings. In various embodiments, the material that is used to make the anchor, i.e., the elongate anchor member(s), the tensioning member, or both, is multilayered. In some embodiments, the material includes a coating of resorbable polymer. In other some embodiments, the materials includes a semipermeable polymer that optionally is impregnated with one or more of the compounds discussed herein. In certain embodiments, the one or more compounds is released in a controlled manner.

In various embodiments, the anchor, including the elongate anchor member(s), the tensioning member, or both, includes one or more compounds that address issues associated with the product performance. For example, one or more compounds can be embedded in the anchor member. In certain embodiments, the one or more compounds are released over time after implantation. These compounds can reduce calcification, protein deposition, thrombus formation, or a combination of some or all of these conditions. The one or more compounds can also be used to stimulate a biological response, for example, to induce tissue in-growth.

In some embodiments, the compound is an anti-inflammatory agent. In some embodiments, the compound reduces tissue proliferation adjacent to the device. One with ordinary skill in the art would understand that numerous agents are available for the above applications and can select such an agent without undue experimentation for each of the applications. As such, anchors having one or more of the numerous agents are within the scope of the present teachings.

In various embodiments, the tensioning member extends through openings along the elongate anchor member as described herein such that tightening the tensioning member will cause the elongate anchor member to fold. Although certain examples of anchor deployment are described herein, one with ordinary skill in the art would appreciate that deployment of the anchor may take on various forms due to the flexible nature of the anchor member, especially when a highly flexible fabric or other materials is used. For example, a fabric material or other similarly flexible materials may be folded or otherwise deformed during a deployment to a leakage site.

Another aspect of the present teachings includes methods of treating a paravalvular leakage. In various embodiments, the method includes providing an anchor as described herein, positioning the anchor through a paravalvular leakage, deploying the anchor where at least a part of the distal portion of the elongate anchor member is on one side of the paravalvular leakage. In various embodiments, the method includes applying tension to the tensioning member so that at least a part of the distal portion of the elongate anchor member transitions from the elongate configuration to the shortened configuration. In various embodiments, the method includes deploying the anchor wherein at least a part of the proximal portion of the elongate anchor member is on the other side of the paravalvular leakage. In various embodiments, the method includes applying tension to the tensioning member so that at least a part of the proximal portion of the elongate anchor member transitions from the elongate configuration to the shortened configuration.

In various embodiments, the method includes providing an anchor as described herein, positioning the anchor through a paravalvular leakage, deploying the anchor where at least a part of a first elongate anchor member is on one side of the paravalvular leakage. In various embodiments, the method includes applying tension to the tensioning member so that at least a part of the first elongate anchor member transitions from the elongate configuration to the shortened configuration. In various embodiments, the method includes deploying the anchor wherein at least a part of a second elongate anchor member is on the other side of the paravalvular leakage. In various embodiments, the method includes applying tension to the tensioning member so that at least a part of the second elongate anchor member transitions from the elongate configuration to the shortened configuration. And in these embodiments, the anchor used in repairing a paravalvular leakage can include two or more elongate anchor members and a tensioning member can pass through one, two, or more of the elongate anchor members.

In various embodiments, anchors of the present teachings is used percutaneously. For example, the anchors are delivered percutaneously. In other embodiments, anchors of the present teachings are used in minimally invasive surgeries. In yet other embodiments, anchors of the present teachings are used in open-heart surgeries.

In various embodiments, the method includes introducing a catheter approximately at the paravalvular leakage site. In some embodiments, the method includes withdrawing the catheter to deploy the anchor where at least a part of the distal portion of the elongate anchor member is on one side of the paravalvular leakage. In some embodiments, the method includes withdrawing the catheter to deploy the anchor wherein at least a part of the proximal portion of the elongate anchor member is on the other side of the paravalvular leakage. In some embodiments, the method includes withdrawing the catheter to deploy the anchor where at least a part of a first elongate anchor member is on one side of the paravalvular leakage. In some embodiments, the method includes withdrawing the catheter to deploy the anchor wherein at least a part of a second elongate anchor member is on the other side of the paravalvular leakage.

In various embodiments, a clinician deploys a plurality of anchors in a paravalvular leakage, when necessary and practical.

In various embodiments, upon deployment, at least half number of the folds is distal to the paravalvular leakage and the rest of the folds are proximal to the paravalvular leakage. In other embodiments, upon deployment, less than half of the folds are distal to the paravalvular leakage and the rest of the folds are proximal to the paravalvular leakage. In yet other embodiments, upon deployment, more than half of the folds are distal to the paravalvular leakage and the rest of the folds are proximal to the paravalvular leakage.

In various embodiments, upon deployment, at least some of the folds is distal to the paravalvular leakage. In various embodiments, upon deployment, at least some of the folds are proximal to the paravalvular leakage. In other embodiments, upon deployment, less than half of the folds are distal to the paravalvular leakage. In other embodiments, upon deployment, less than half of the folds are proximal to the paravalvular leakage. In yet other embodiments, upon deployment, more than half of the folds are distal to the paravalvular leakage. In yet other embodiments, upon deployment, more than half of the folds are proximal to the paravalvular leakage.

In various embodiments, upon deployment, at least one of the folds is in the paravalvular leakage. In some embodiments, upon deployment, at least some of the folds are distal to the paravalvular leakage and at least one of the folds is in the paravalvular leakage. In some embodiments, at least some of the folds are proximal to the paravalvular leakage and at least one of the folds is in the paravalvular leakage. In certain embodiments, upon deployment, at least some of the folds are distal to the paravalvular leakage, at least one of the folds is in the paravalvular leakage, and at least some of the folds are proximal to the paravalvular leakage.

In various embodiments, upon deployment, at least a part of a first anchor member is distal to the paravalvular leakage. In various embodiments, upon deployment, at least a part of a second anchor member is proximal to the paravalvular leakage. In various embodiments, upon deployment, at least a part of an anchor member is in the paravalvular leakage. In some embodiments, upon deployment, at least a part of a first anchor member is distal to the paravalvular leakage and at least a part of a second anchor member is proximal to the paravalvular leakage. In certain embodiments, upon deployment, at least a part of a first anchor member is distal to the paravalvular leakage, at least a part of a second anchor member is proximal to the paravalvular leakage, and at least a part of a third anchor member is in the paravalvular leakage.

In various embodiments, the elongate anchor member also includes a marker. The marker can be in the form of threads, beads, or other forms. Without limiting the scope of the present teachings, the marker allows the anchor member to be visualized by using a radiographic imaging equipment using x-ray, magnetic resonance, ultrasound, fluoroscopic, or other visualization techniques. In some embodiments, markers are attached to the anchor member. For example, the markers can be wrapped, laminated, and/or bonded through a welding process. An adhesive such as cyanoacrylate or other adhesives known to those skilled in the art can also be used to attach a marker to the anchor member.

In some embodiments, the marker is a radiopaque marker. In certain embodiments, the radiopaque marker is made of titanium, tungsten, platinum, irridium, gold, an alloy of any of these materials, or a composite having any of the above materials. Other materials that are known to those skilled in the art can also be used.

In some embodiments, the marker is a paramagnetic marker. In certain embodiments, the paramagnetic marker is made of a material containing gadolinium, iron, platinum, manganese, cobalt, fluorine, or other paramagnetic materials. In yet other embodiments, the markers each comprises other MR visible materials that are known to those skilled in the arts.

In some embodiments, the marker is an echogenic marker. In certain embodiments, the echogenic marker is made of a material that is capable of reflecting increased ultrasound waves. Some echogenic materials are described herein elsewhere.

In various embodiments, the marker protrudes out of or is flush with the anchor. In various embodiments, the markers are arranged on the implant in a pattern.

In various embodiments, the anchor or a component thereof is treated so that the anchor or a part thereof is visible under a visualization technique. In some embodiments, the visualization technique is based on ultrasound. For example, the visualization technique is echocardiography. In some embodiments, an elongate anchor member of the present teachings is treated so that it is visible in a visualization technique. In certain embodiments, a part of the elongate anchor member is treated so that it is visible in a visualization technique. In some embodiments, a marker of the present teachings is treated so that it is visible in a visualization technique. In some embodiments, the treatment is performed on a surface of an anchor or a component thereof. In certain embodiments, a surface of at least a part of the elongate anchor member is treated so that the elongate anchor member is visible in a visualization technique. In certain embodiments, a surface of at least a part of the marker is treated so that the marker is visible in a visualization technique.

In various embodiments, the treatment is performed with an echogenic material. For example, the material can contain fluorine element. In some embodiments, the material includes a perfluoro compound. In certain embodiments, the material includes perflutren. In certain embodiments, the material includes perflexane. In certain embodiments, the material includes sulfur hexafluoride. In other embodiments, the material includes another echogenic material known to persons with ordinary skill in the art.

In various embodiments, the method includes locating a paravalvular leakage. For example, a paravalvular leakage can be detected and/or located by using echocardiography, computed tomography (CT), or cardiac magnetic resonance. In some embodiments, the method includes locating a paravalvular leakage by using echocardiography.

Yet another aspect of the present teachings includes a device used to treat a paravalvular leakage. In various embodiments, the device includes a catheter and an anchor as described herein. In some embodiments, the catheter includes a distal end and a lumen having an opening at the distal end. In some embodiments, the anchor is provided at least partially in the lumen.

BRIEF DESCRIPTION OF DRAWINGS

Without wishing to narrow the scope of the enclosed claims, the present teachings may best be understood by reference to the following description taken in conjunction with the accompanying drawings in which:

FIG. 3I is a side view similar to FIG. 3B, but showing the distal portion of the exemplary anchor fully compressed and engaged against the paravalvular leakage, FIG. 3J is a side view similar to FIG. 3C but illustrating the proximal portion of the exemplary anchor being moved toward the paravalvular leakage, FIG. 3K is a side view similar to FIG. 3C but illustrating the proximal portion of the exemplary anchor being moved toward the paravalvular leakage, FIG. 3L is an enlarged cross sectional view of an exemplary anchor fully deployed and fastened with a paravalvular leakage between proximal and distal anchor portions, FIG. 7A is a perspective view of an anchor in accordance with some embodiments of the present teachings, FIG. 7B is a perspective view of an anchor in accordance with some embodiments of the present teachings, FIG. 7C is a perspective view of an anchor in accordance with some embodiments of the present teachings, FIG. 10A is a perspective view of an anchor in accordance with some embodiments of the present teachings, FIG. 10B is a side elevation view of the anchor in FIG. 10A.

DETAILED DESCRIPTION

Figure 1:
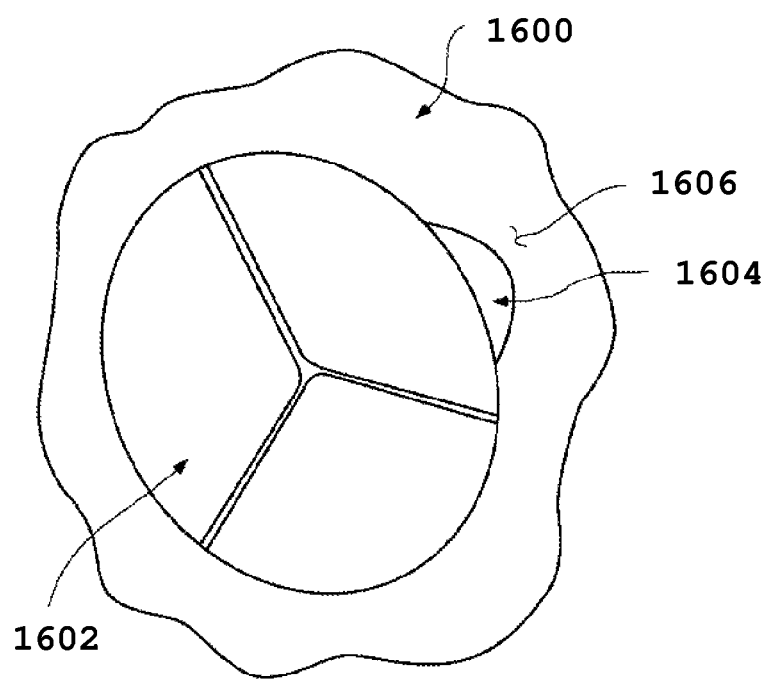
FIG. 1 shows an artificial valve implanted into a heart having a paravalvular leakage.

Certain specific details are set forth in the following description and Figures to provide an understanding of various embodiments of the present teachings. Those of ordinary skill in the relevant art will understand that various features of the present teachings may be used alone or in numerous combinations depending on the needs and preferences of the user. Those skilled in the art can also practice other embodiments of the present teachings without one or more of the details described below. Thus, it is not the intention of the present teachings to restrict or in any way limit the scope of the appended claims to such details. While various processes are described with reference to steps and sequences in the following disclosure, the steps and sequences of steps should not be taken as required to practice all embodiments of the present teachings.

As used herein, the term "proximal" means closest to the operator (less into the body) and "distal" means furthest from the operator (further into the body). In positioning a medical device from a downstream access point, distal is more upstream and proximal is more downstream.

As used herein, the term "tensioning member" means a member which can take forms of a suture, cable, wire, or any other small diameter, flexible, semi-rigid or rigid material having a suitable tensile strength for the intended use. In addition, as used herein, the term "wire" can be a strand, a cord, a fiber, a yarn, a filament, a cable, a thread, or the like, and these terms may be used interchangeably.

The term "suture" used herein can be a strand, a wire, a cord, a fiber, a yarn, a filament, a cable, a thread, or the like, and these terms may be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

It will be appreciated that like reference numerals are used herein to refer to like elements in all embodiments and reference numerals with prime marks (') or double prime marks (") refer to like elements that have been modified in a manner as described herein or otherwise shown in the associated Figure.

Figure 2:
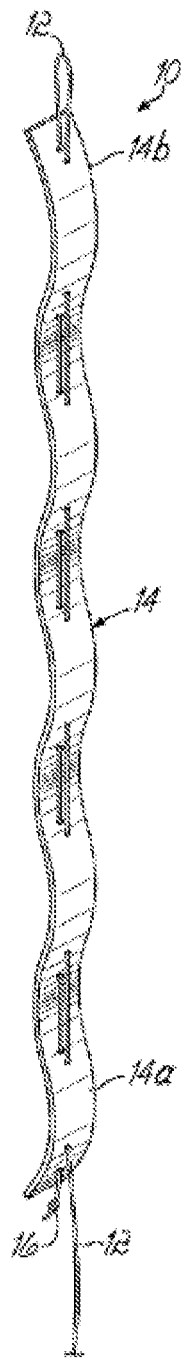
FIG. 2 is a perspective view of an exemplary anchor in accordance with the present teachings.

Referring first to FIG. 2, an anchor 10 constructed in accordance with some embodiments of the present teachings generally includes a tensioning member 12, such as a suture, extending through spaced apart points along an elongate anchor member 14 of flexible material, such as a surgical grade fabric. It will be appreciated that the tensioning member 12 may take other forms other than suture material, such as cable or any other small diameter member having a high enough tensile strength for the intended use. The elongate anchor member 14 may also take various forms such as woven or nonwoven fabrics, polymers, metals, or other suitable materials or combinations of materials. One or more separate pledgets or other securement members (not shown) may be used in conjunction with the elongate anchor member 14 for added securement and/or concealing the elongate anchor member 14 and, for example, thereby inhibiting blood clotting within or adjacent to the folds that will be formed in the elongate anchor member 14.

A woven or nonwoven material may contain additional materials, such as threads, beads or other elements that cause at least portions of the elongate anchor member 14 to be radiopaque. Currently, a surgical grade fabric constructed from polyester, such as Dacron®, is contemplated for use in constructing the elongate anchor member 14. One of many possible alternative materials for use in constructing the elongate anchor member 14 is polytetrafluoroethylene (PTFE). Anchor 10 may be partly or wholly formed from materials that are absorbed into the patient's tissue over time, depending on the intended use. The edges and/or other portions of the elongate anchor member 14 may be suitably modified to prevent fraying, such as by being coated with a material that locks the fibers in place, or otherwise modified in a manner that locks the fibers at least at the edges of the elongate anchor member 14 in place.

The suture 12 may extend from a proximal portion 14a of the elongate anchor member 14 to a distal end portion 14b and then loop back through spaced apart points of the elongate anchor member 14 to the proximal portion 14a where a knot 16 or other stop member is located. As will become apparent, the suture 12 extends through spaced apart locations along the elongate anchor member 14 such that tensioning of the suture 12 or other tensioning member will cause the elongate anchor member 14 to form folded portions 14c when the tensioning member 12 is placed under tension or pulled. Thus, the elongate anchor member 14 is activated in this manner between essentially an elongate configuration, such as shown in FIG. 2, and a shortened configuration, such as a folded or otherwise shortened configuration having an expanded width in at least one dimension as compared to the elongate configuration. It will be appreciated that the deployment orientation may take on various forms due to the flexible nature of the elongate anchor member 14, especially when using a highly flexible fabric or other material. For example, a fabric material or other similarly flexible materials may be folded or otherwise deformed for carrying purposes within a catheter and/or during deployment to a paravalvular leakage site and then suitably activated at the leakage site.

Figure 3A:
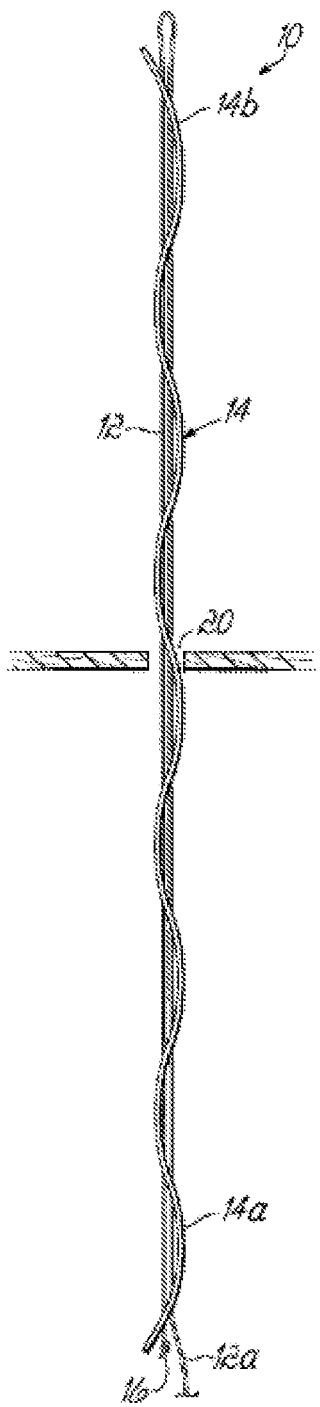
FIG. 3A is a side view of an anchor positioned in a paravalvular leakage in accordance with some embodiments of the present teachings.
Figure 3B:
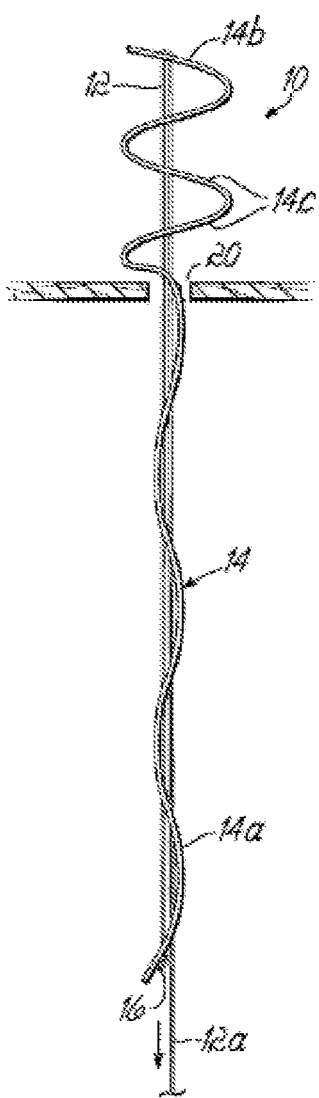
FIG. 3B is a side view similar to FIG. 3A, but illustrating the distal portion of the exemplary anchor being moved toward the paravalvular leakage.
Figure 3C:
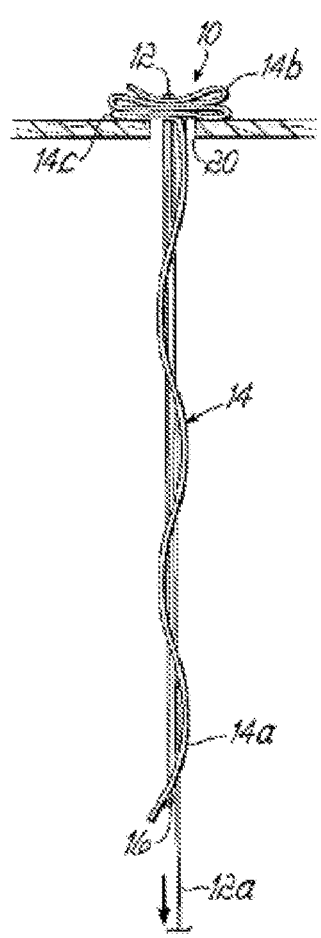
FIG. 3C is a side view similar to FIG. 3B, but showing the distal portion of the exemplary anchor fully compressed and engaged against the paravalvular leakage.
Figure 3D:
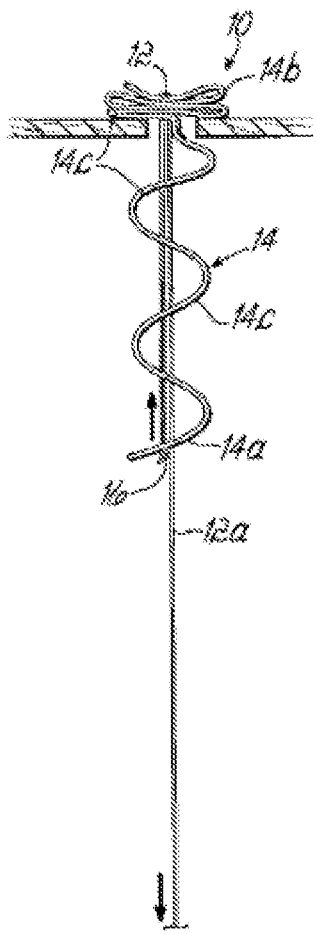
FIG. 3D is a side view similar to FIG. 3C but illustrating the proximal portion of the exemplary anchor being moved toward the paravalvular leakage.
Figure 3E:
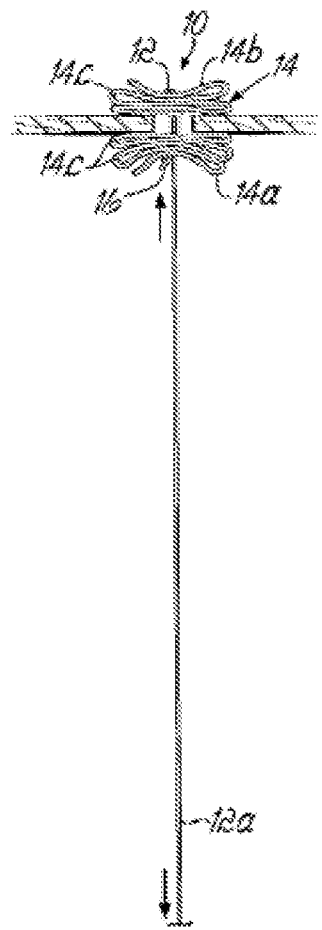
FIG. 3E illustrates the proximal and distal portions of the exemplary anchor fully compressed against opposite sides of the paravalvular leakage.
Figure 3F:
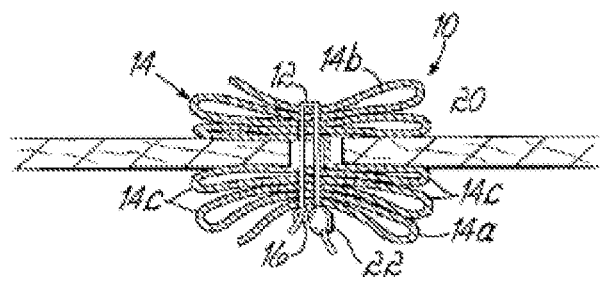
FIG. 3F is an enlarged cross sectional view of an exemplary anchor fully deployed and fastened with a paravalvular leakage between proximal and distal anchor portions.

More specifically referring to FIGS. 3A-3E, the elongate anchor member 14 and attached suture 12 are initially inserted through a paravalvular leakage site 20 as generally shown in FIG. 3A. One end or portion 12a of the suture 12 is then pulled and thereby placed under tension. It will be appreciated that, for catheter-based procedures, suture portion 12a may extend to a location outside the patient's body for pulling or tensioning, or it may be grasped by a suitable mechanism within the catheter and pulled or tensioned. Pulling suture portion 12a may initially draw the distal portion 14b of the elongate anchor member 14 toward the paravalvular leakage site 20 as shown in FIG. 3B. Once the distal portion 14b is compressed against the leakage site 20, the proximal portion 14a begins to be drawn and compressed against a proximal side of the paravalvular leakage site 20 as shown in FIGS. 3C-3E. This occurs because end 12a of the suture 12 is being pulled downwardly (as viewed for purposes of discussion in FIGS. 3C-3E) and, since the suture 12 is looped in a reverse direction through distal end portion 14b of the elongate anchor member 14, the knot 16 at the end of the suture 12 moves upwardly and brings the proximal portion 14a of the elongate anchor member 14 with it. In this manner, the proximal portion 14a of the elongate anchor member 14 is being folded and drawn along the suture 12 toward the paravalvular leakage 20 and then firmly compressed against the proximal side of the paravalvular leakage 20 as shown in FIG. 3E. As further shown in FIG. 3F, a suitable locker element, such as a crimp member 22, a knot or other element may be used to maintain the suture 12 and elongate anchor member 14 in the positions shown in FIG. 3F securely anchoring the proximal and distal portions 14a, 14b of the elongate anchor member 14 folded against opposite sides of the paravalvular leakage 20.

Figures 3G, 3H:
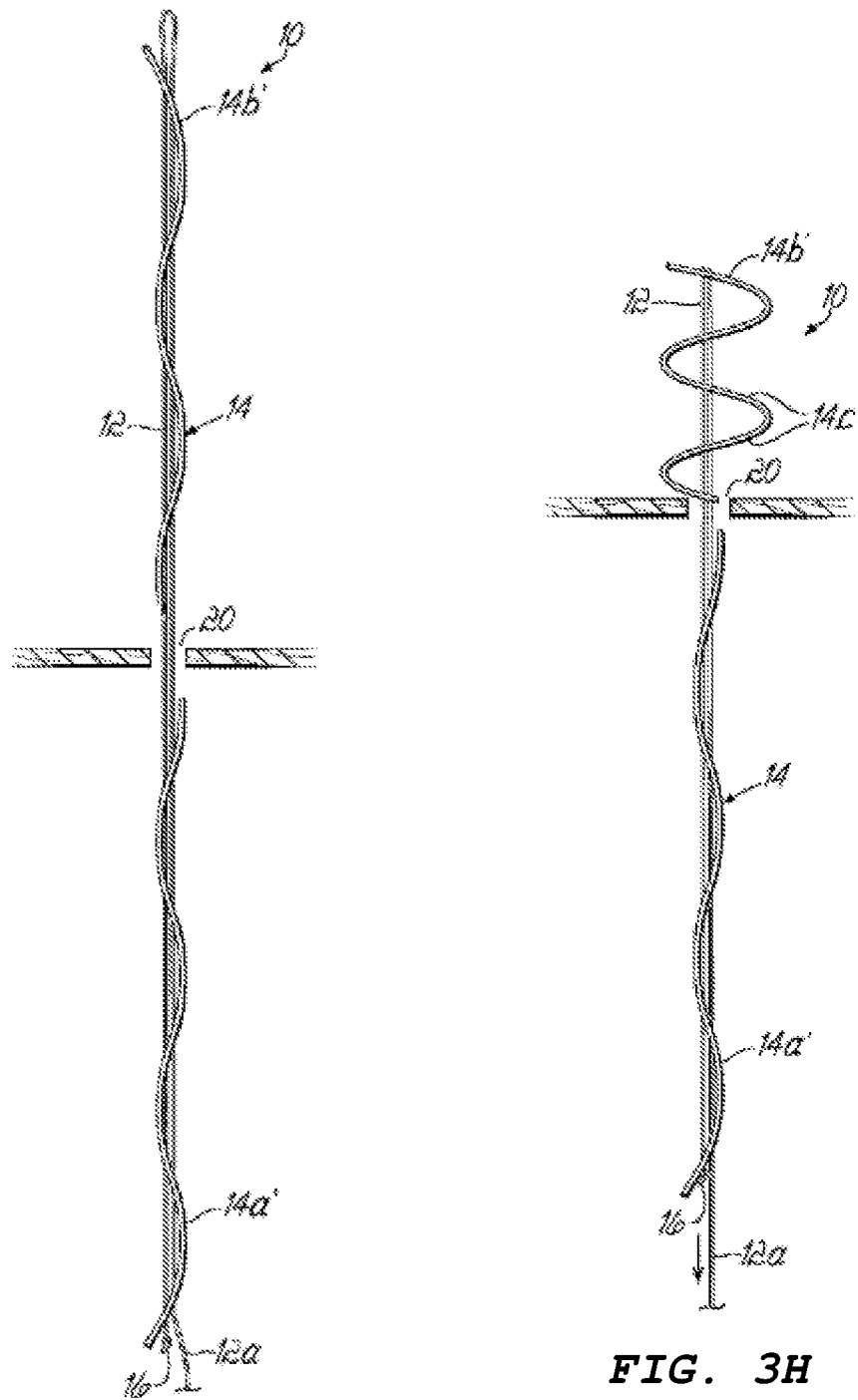
FIG. 3G is a side view of an anchor positioned in a paravalvular leakage in accordance with some embodiments of the present teachings.
FIG. 3H is a side view similar to FIG. 3A, but illustrating the distal portion of the exemplary anchor being moved toward the paravalvular leakage.

Anchors having two or more elongate anchor members can also be used to repair a paravalvular leakage. Thus, as shown in FIG. 3G, in various embodiments, an anchor includes a distal elongate anchor member 14b', a proximal elongate anchor member 14a', and a tensioning member 12 slideably connecting the distal elongate anchor member 14b' and the proximal elongate anchor member 14a'. In some embodiments, one end of the tensioning member passes through the proximal elongate anchor member 14a' and the distal elongate anchor member 14b', loops back, passes through the distal elongate anchor member 14b' and the proximal elongate anchor member 14a', and forms a knot 16 around the tensioning member 12. In certain embodiments, the other end, or the proximal end 12a', of the tensioning member extends through a delivery catheter and exists outside of the body. The passing through an elongate anchor member can be achieved by passing through one or two holes in the elongate anchor member or threading through the elongate anchor member itself.

Thus, the method of repairing a paravalvular leakage, in some embodiments, includes, as shown in FIG. 3G, inserting the distal elongate anchor member 14b' and attached tensioning member 12 through a paravalvular leakage 20. In some embodiments, the method includes pulling the proximal end 12a of the tensioning member 12. The pulling of the tensioning member, in some embodiments, folds at least a portion of the distal elongate anchor member 14b' and/or draws the distal elongate anchor member towards the paravalvular leakage site 20, as shown FIG. 3H. In some embodiments, the method includes continuing pulling the proximal end 12a of the tensioning member 12 to compress the distal elongate anchor member 14b' against the paravalvular leakage 20, as shown in FIG. 3I. In some embodiments, the method includes folding at least a portion of the proximal elongate anchor member 14a' and drawing the proximal elongate anchor member 14a' towards the paravalvular leakage site 20, as shown in FIG. 3J. The folding of at least a portion of the proximal elongate anchor member 14a' and/or the drawing of the proximal elongate anchor member 14a', in certain embodiments, are achieved sequentially or simultaneously by continuing pulling the proximal end 12a of the tensioning member 12. As the distal elongate anchor member 14b' and the proximal elongate anchor member 14a' are compressed against the paravalvular leakage 20, in some embodiments, the method includes using a suitable locker element 22 to maintain the anchor 10 in the deployed configuration, as shown in FIG. 3L.

Figures 4, 5A:
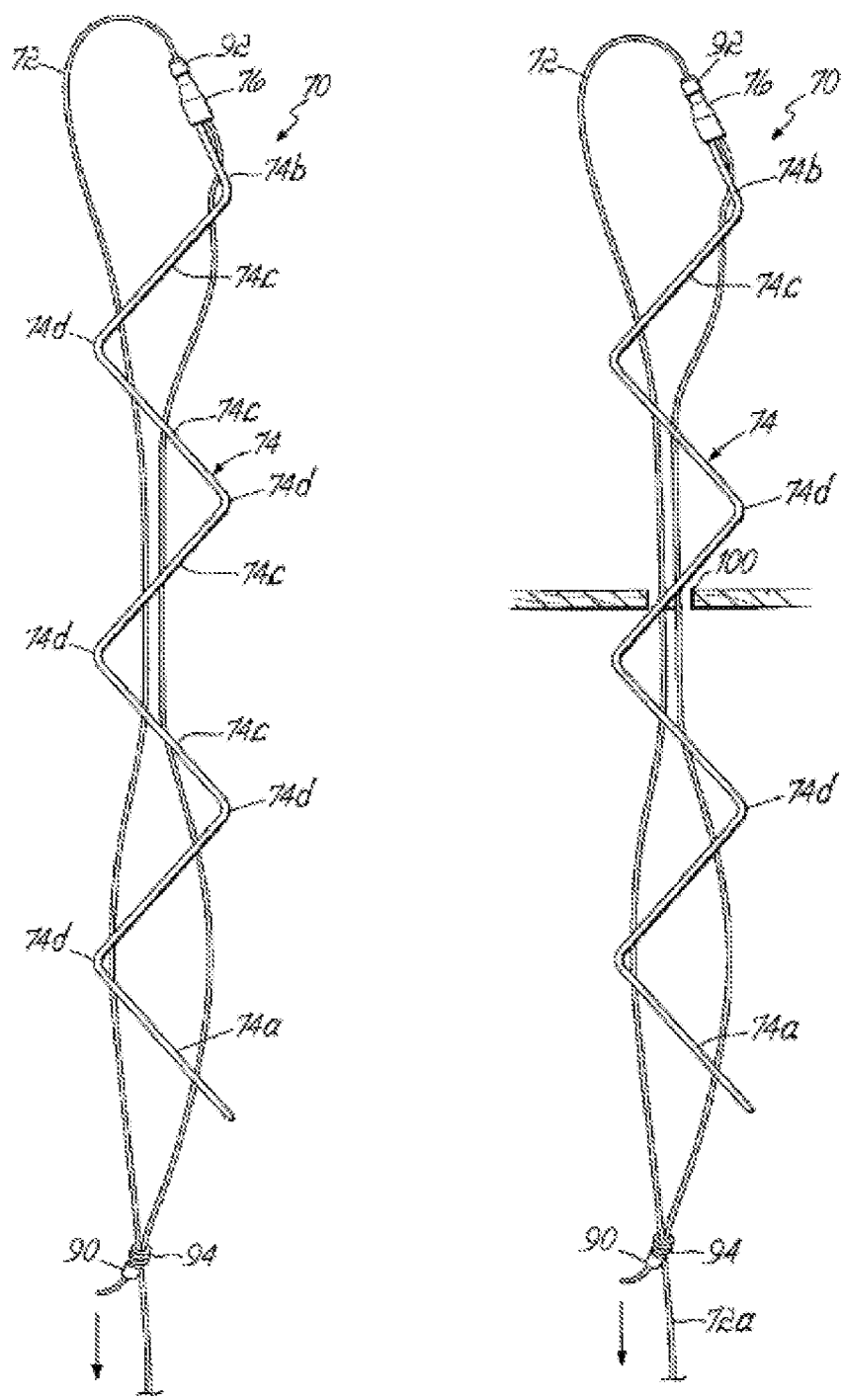
FIG. 4 is a side elevation view of an exemplary anchor in accordance with some embodiments of the present teachings.
FIGS. 5A-5D are respective side views illustrating a sequence of steps used for securing the anchor to a paravalvular leakage in accordance with some embodiments of the present teachings.

FIG. 4 is a side elevation view of an anchor 70 according to some embodiments of the present teachings. This anchor includes a distal tip 76. In addition, this anchor includes a proximal radiopaque band 90 and a distal radiopaque band 92. Both the radiopaque bands can be attached to the suture 72, as shown in FIG. 4, or otherwise secured to the suture 72, at the proximal end portion of the anchor member 74 and to either the interior or exterior of the distal tip 76, respectively, or any other part of the anchor 70. Without wishing to be bound by any particular theory, under a fluoroscope, these bands or other markers 90 and 92 will indicate to the clinician that the anchor 70 has been deployed, activated, fully compressed, and/or fastened, as necessary during the procedure.

The tip 76 itself may alternatively be formed from a radiopaque material. In this embodiment, the knot 94 formed in the suture 72 or other tensioning member is a slip knot through which another portion of the suture 72 slides during activation of the anchor 70. It will be appreciated that this slip knot 94 may be replaced by another element which serves substantially or approximately the same purpose but takes the form, for example, of a small tubular element or other feature similar in function to a slip knot.

In various embodiments, the elongate anchor member 74 may be about 40 mm long by about 3 mm wide. This may be desirable to achieve a lower profile. These embodiments may lead to more versatile applications, lower incidents of blood clotting, easier use, etc. Of course, any other desired dimensions and shapes may be used, depending on application needs.

Figure 6A:
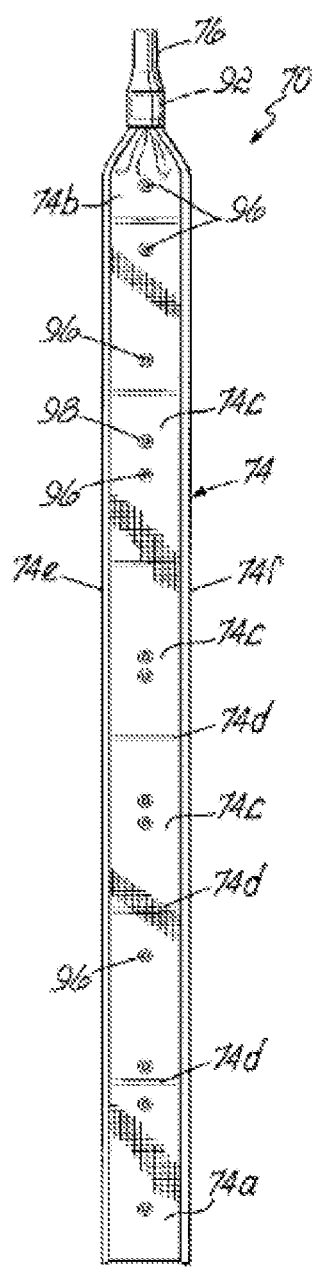
FIG. 6A is a front view of the elongate anchor member of an anchor in accordance with some embodiments of the present teachings.

As further shown in FIGS. 4 and 6A, the tensioning member or suture 72 can advantageously extend through respective fold portions 74c of the elongate anchor member 74 in essentially an hourglass configuration. Specifically, adjacent portions of the suture 72 located near the proximal and distal end portions 74a, 74b of the anchor member 74 are spaced farther apart than the adjacent portions of the suture 72 in the middle of the anchor member 74.

Figure 6B:
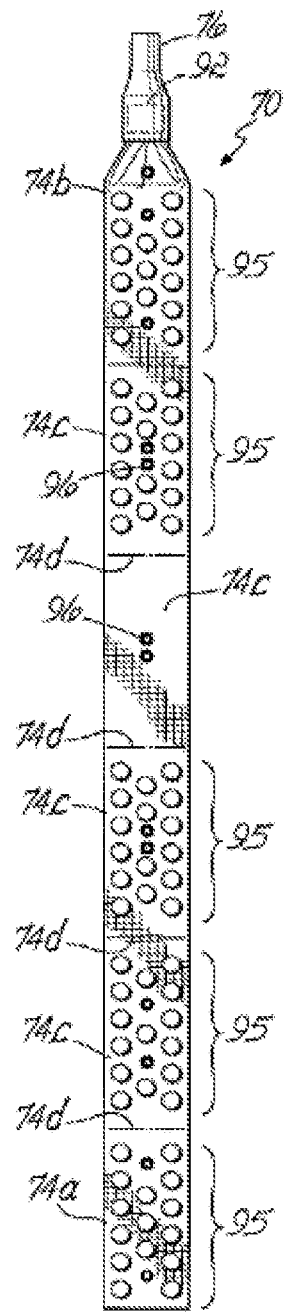
FIG. 6B is a front elevation view similar to FIG. 6A, but illustrating radiopaque markers in accordance with some embodiments of the present teachings.

As further shown in FIG. 6B, radiopaque markers, such as distinct areas of dots 95, may be used for enabling the clinician to visualize the folds of the elongate anchor member 74 during deployment and securement of the elongate anchor member 74. These dots or other radiopaque markers may be printed on the anchor member 74. For example, dots 95 or other markers may be formed with a platinum powder base ink or other suitable material that is radiopaque and biologically compatible. This radiopaque material may also add stiffness to the fold sections 74c thereby helping to maintain the fold sections 74c flat and increasing retention force on the paravalvular leakage. Meanwhile, the fold lines 74d between fold sections 74c can remain highly flexible to create tight radius fold lines.

As further shown in FIG. 6A, each of the holes 96 that the tensioning member or suture 72 is received through may be marked by circles 98 surrounding each hole 96 or other markers for visualizing purposes during assembly of the tensioning member or suture 72 with the elongate anchor member 74. Optionally, holes 96 may be eliminated and the suture 72 may be threaded with a needle through the anchor member 74. One could also, for example, choose different sets of holes 96 along anchor member 74 for receiving the tensioning member or suture 72 thereby changing the width of the folds and/or number of folds and/or shape of the folds depending on the application needs or desires of the clinician.

The tensioning member or suture 72 may be threaded or otherwise attached along the anchor member 74 in any number of manners including, for example, x-patterns or other crossing patterns, zig-zag patterns, etc. that may alter the folded or otherwise shortened or compressed footprint of the anchor into various beneficial shapes, such as flower shapes, circular shapes or other rounded shapes, ball shapes or other configurations. Modifications of the manner in which the tensioning member or suture 72 is threaded or otherwise attached along the length of anchor member 74 may result in higher or lower tensioning force being required to compress the anchor and/or higher or lower friction holding force that may help maintain the anchor in the compressed or shortened configuration.

Figure 6C:
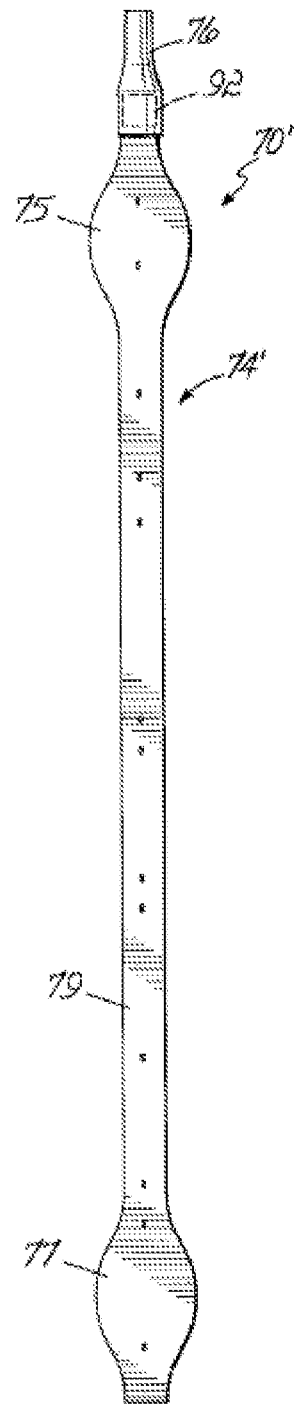
FIG. 6C is a front elevation view of an alternative elongate anchor member having a varying width along its length in accordance with some embodiments of the present teachings.

The width of the elongate anchor member 74' may be varied along its length, such as by tapering, stepping, or forming an hourglass shape or shapes along the length of the anchor member 14. For example, as illustrated in FIG. 6C, having proximal and distal end portions 75, 77 of wider dimension than an intermediate or middle portion or portions 79 along the length of anchor member 74' will allow these wider portions 75, 77 may cover over the more intermediate folded portions 79 and prevent unnecessary contact with adjacent tissue during use.

Figure 6D:
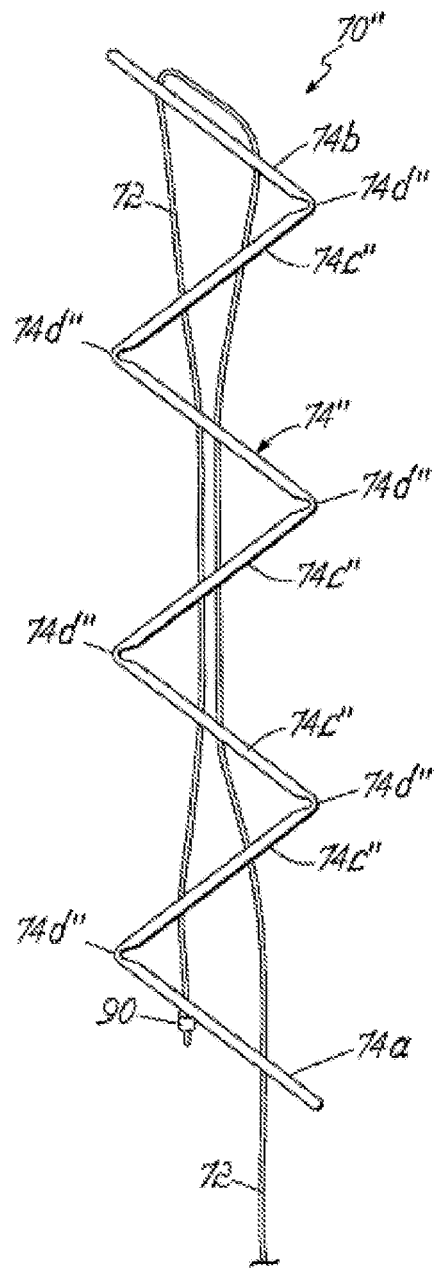
FIG. 6D is a side elevation view of another alternative elongate anchor member utilizing more rigid fold sections separated by living hinges in accordance with some embodiments of the present teachings.

The elongate anchor member 74 may have variable stiffness including, for example, a relatively rigid perimeter or relatively rigid edges 74e, 74f (FIG. 6A) or intermittent relatively rigid sections 74c" separated by flexible sections such as living hinges 74d" (FIG. 6D) that may aid in folding and securing the elongate anchor member 74" into a folded condition.

Figure 5B:
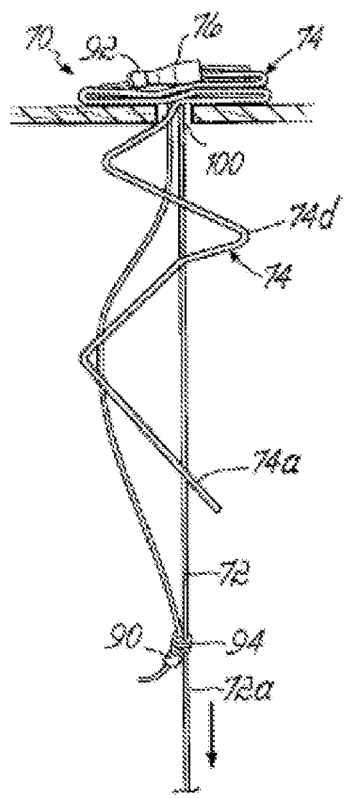
Figure 5C:
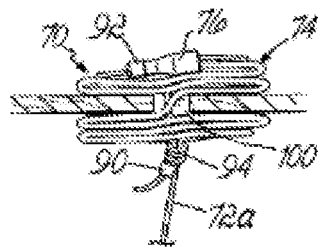
Figure 5E:
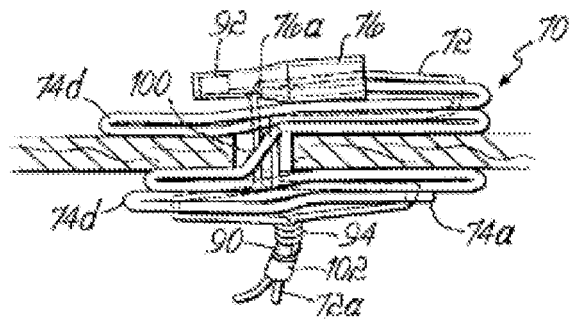
FIG. 5E is a view similar to FIG. 5D, but illustrating an alternative tip and tensioning member arrangement in accordance with some embodiments of the present teachings.
Figure 5D:
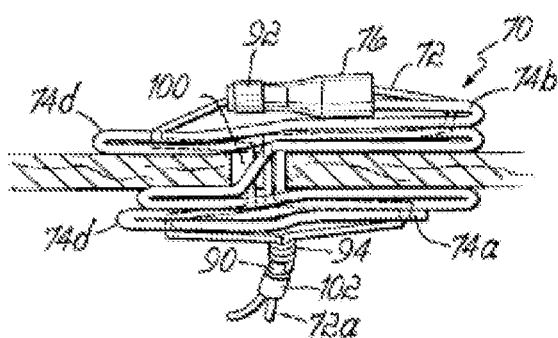

FIGS. 5A-5D illustrate a series of steps for deploying and securely fastening the anchor 70 to a paravalvular leakage site 100 according to some embodiments of the present teachings. Generally, as shown in FIG. 5A, the combination of the elongate anchor member 74 and tensioning member or suture 72 is deployed through the paravalvular leakage site 100. One end or portion 72a of the suture 72 that extends through the slip knot 94 is then pulled. This causes the distal portion 74b of the elongate anchor member 74 to fold and compress against the distal side of the paravalvular leakage 100. As shown in FIG. 5B, further pulling the tensioning member 72 causes the slip knot 94 to ride upwardly or distally along the suture 72 and against a proximal portion 74a of the elongate anchor member 74, thereby folding and compressing the proximal portion 74a against the proximal side of the paravalvular leakage 100 as shown in FIG. 5C. As shown in FIG. 5D, a suitable crimp or locking element 102 may be used to securely lock the slip knot 94 in place relative to the suture or tensioning member segment which extends therethrough. This will lock the entire anchor 70 in place with the respective proximal and distal folded anchor member portions 74a, 74b securely retaining the paravalvular leakage 100 therebetween. FIG. 5D shows the tip 76 acting as a retainer on top of the distal end portion 74b to assist in holding the distal end portion 74b in place.

FIG. 5E shows an alternative in which the tensioning member is threaded through at least one hole 76a more centrally located in the tip. Yet another alternative would be to thread the tensioning member through two centrally located holes instead of through the proximal end of the tip 76 and one centrally located hole 76a as shown in FIG. 5E. These alternatives allow the tip 76 to act more like a "T"-bar with forces acting in a more perpendicular or normal manner relative to the distal end portion 74b of the anchor member 74.

FIG. 7A illustrates an exemplary anchor of the present teachings. In various embodiments, the elongate anchor member has a rectangle profile as illustrated in FIG. 7A. In other embodiments, the elongate anchor member has an hour glass profile as illustrated in FIG. 7B. One skilled in the art would understand that the elongate anchor member can have other profiles, and accordingly, the embodiments discussed herein are not limiting to the scope of the present teachings.

Referring to FIG. 7A, an anchor 200 constructed in accordance with some embodiments of the present teachings generally includes a tensioning member 201 extending from a proximal end portion 212 of an elongate anchor member 210 to a distal end portion 214. In some embodiments, the tensioning member 201 loops back and extends from the distal end 214 to the proximal end portion 212. In some embodiments, the tensioning member 201 passes through a plurality of openings along the elongate anchor member 210. In some embodiments, one end of the tensioning member 201, after it extends from the proximal end to the distal end and loops back to the proximal end of the anchor member 210, forms a knot 220 around the other end portion of the tensioning member 201. In some embodiments, the knot 220 slides along the other end portion of the tensioning member 201 in such way that it pulls the free end of the tensioning member 201 proximally, causing the knot 220 moving distally and shortening the longitudinal length of the anchor member 210. By doing so in these embodiments, the elongate anchor member 210 is folded and the ends of the anchor member 210 are drawn toward each other. In certain embodiments, the elongate anchor member 210 also can include at least one pre-set folding line (not shown) which allows the elongate anchor member 210 to be fold at the pre-set folding line.

In various embodiments, an anchor, such as that referred to as anchor 200, shortens at one of the proximal and distal ends. For example, when the tensioning member 201 is pulled, at least a part of the distal portion 214 folds first while the proximal end 212 substantially maintains its elongated configuration. In some embodiments, this occurs when the distal portion 214 is deployed. In certain embodiments, this occurs when the distal portion 214 is deployed and the proximal portion 212 is not deployed, for example, because the proximal portion 212 is restrained in a delivery catheter (not shown). In other embodiments, when the tensioning member 201 is pulled, at least a part of the proximal portion 212 folds first while the distal portion 214 substantially maintains its elongated configuration. It will be appreciated by a person with ordinary skill in the art that an anchor of the present teachings may also be folded in a sequential manner under other circumstances.

As seen in FIG. 7A, in various embodiments, the elongate anchor member has two sets of openings 225, 226 (first openings 225 and second openings 226). In some embodiments, the tensioning member 201 extends from the proximal end portion 212 of the anchor member 210 to the distal end portion 214 of the anchor member 210 through the first set of openings 225. Upon reaching the distal end of the elongate anchor member 210, in some embodiments, the tensioning member 201 loops back and further extends from the distal end portion of the anchor member 210 to the proximal end of the anchor member through the second set of openings 226.

In certain embodiments, as shown in FIG. 7A, the tensioning member 201 extends from the proximal end of the anchor member 210 distally, travels from one side of the anchor member 210 to another side by passing through the first opening 225 closest to the proximal end of the anchor member 210 in the first set of openings 225; the tensioning member 201 further extends distally, passes through the next opening 225 distal to the first opening 225 in the first set of openings 225. The tensioning member extends further distally repeating above steps until it passes through the last opening 225 in the first set of openings 225 and reaches the distal end of the anchor member 210. In one embodiment of the present teachings, there are ten openings 225 in the first set of openings 225. Anchor members 210 having between four and twelve openings 225 in the first set of openings can be made and used by one with ordinary skill in the art without undue experimentation.

In various embodiments of the present teachings, upon reaching the distal end of the anchor member 210, the tensioning member 201 loops back, extends proximally, travels from one side of the anchor member 210 to another side by passing through the first opening 226 closest to the distal end of the anchor member 210 in the second set of openings 226. The tensioning member 201 further extends proximally, travels to the first side of the anchor member 210 by passing through the next opening 226 proximal to the first opening 226 in the second set of openings 226. The tensioning member 201 extends further proximally repeating the above steps until it passes through the last opening 226 in the second set of openings 226 and reaches the proximal end of the anchor member 210. In some embodiments of the present teachings, there are ten openings 226 in the second set of openings 226. Elongate anchor members 210 having between four and twelve openings 226 in this set can be made and used by one with ordinary skill in the art without undue experimentation.

In various embodiments of the present teachings, as illustrated in FIG. 7A, the tensioning member 201 extends from one side of the anchor member 210 distally, loops back, and ends on the same side of the anchor member 210. In other embodiments, the tensioning member 201 extends from one side of the anchor member 210 distally, loops back, and ends on a different side of the anchor member 210.

In various embodiments of the present teachings, the number of openings 225 in the first set and the number of openings 226 in the second set are the same as illustrated in FIG. 7A. In other embodiments, the number of openings 225 in the first set and the number of openings 226 in the second set are different.

In some embodiments, the first and second sets of openings 225, 226 are different as illustrated in FIG. 7A. In other embodiments, the first and second sets of openings 225, 226 share at least one opening as illustrated in FIG. 7C. This common opening is identified with reference character 227 in FIG. 7C.

As mentioned above, the anchor member 210 can have an hour glass profile as illustrated in FIG. 7B. In this embodiment, the anchor member 210 has a pair of sections 229 of increased width (with one being located at the proximal end portion 212 and one at the distal end portion 214).

According to various embodiments of the present teachings, at least one opening 225 in the first set of openings 225 has a corresponding opening 226 in the second set of openings 226 and together they form a pair of openings on the anchor members 210. In some embodiments, at least one pair of openings 225, 226 form a line perpendicular to the longitudinal axis of the anchor member 210. In other embodiments, at least one pair of the openings 225, 226 forms a line parallel to the longitudinal axis of the anchor member 210. In yet other embodiments, at least one pair of the openings 225, 226 form a line that forms an angle with the longitudinal axis of the anchor member 210. In some embodiments, lines formed by all of the pairs of openings 225, 226 are in the same orientation with one another. For example, they can be parallel to one another and/or perpendicular to the longitudinal axis of the anchor member 210 as illustrated in FIG. 7A. In another embodiment, they can all be parallel to the longitudinal axis of the anchor member 210. In yet other embodiments, the lines formed by all the pairs of openings 225, 226 can have random directions.

In various embodiments, the two openings 225, 226 in a pair are 2-3 mm apart from each other. In some embodiments, the distance between two opening 225, 226 is the same in each pair. In some embodiments, the distance between two openings 225, 226 is different from one pair to another.

In various embodiments, the distance between two adjacent openings 225, 225 (or 226, 226) in the same set, defined by the distance from one opening to the next closest one in the same set of openings (either 225 or 226), is about 5-12 mm. In some embodiments, the distances between each adjacent openings 225, 225 (or 226, 226) is the same as each other. In some embodiments, the distances between each adjacent openings is different from each other.

In various embodiments, at least one pair of the openings 225, 226 are at the lateral center of the anchor member. In some embodiments, all the pairs of openings 225, 226 are at the lateral center of the anchor member. In some embodiments, at least one pair of the openings 225, 226 is biased toward one side of the anchor member 210. In some embodiments, all the pairs of openings 225, 226 are biased toward the same side of the anchor member. In some embodiments, each of the pairs of openings is biased toward different sides of the anchor member 210.

In various embodiments, all the openings 225, 226 in at least one set of openings, or in both the sets of openings, form a straight line. In various embodiments, all the openings in at least one set of the openings, or in both the sets of openings, form a curved line.

Figure 8:
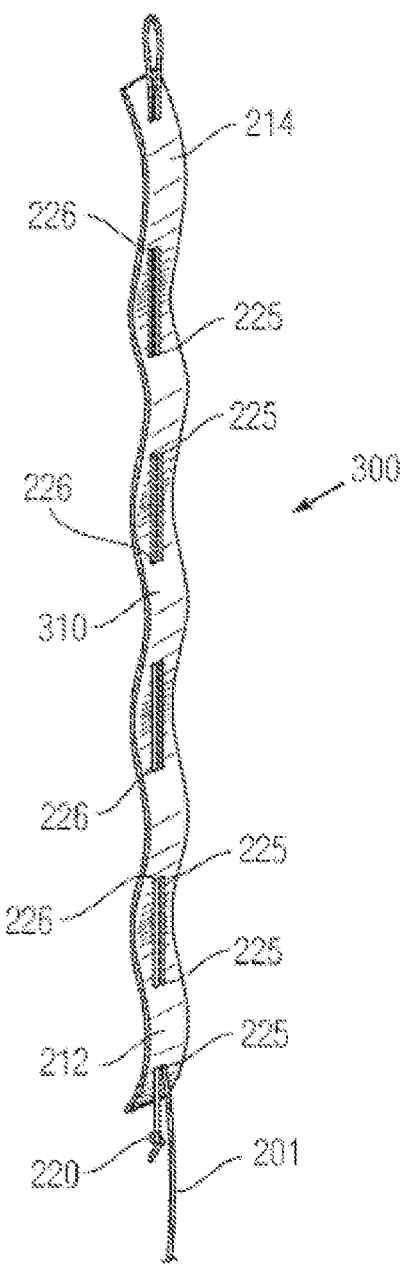
FIG. 8 is a perspective view of an anchor in accordance with some embodiments of the present teachings.

FIG. 8 illustrates an exemplary elongate profile of an exemplary anchor 300 that includes an elongate anchor member 310 and wherein the openings 225 in the first set of openings 225 form a straight line parallel to the longitudinal axis of the anchor member 310, and the openings 226 in the second set of openings 226 form another straight line parallel to the longitudinal axis of the anchor member 310 and at a distance from the line formed by the first set of openings 225.

Figure 9:
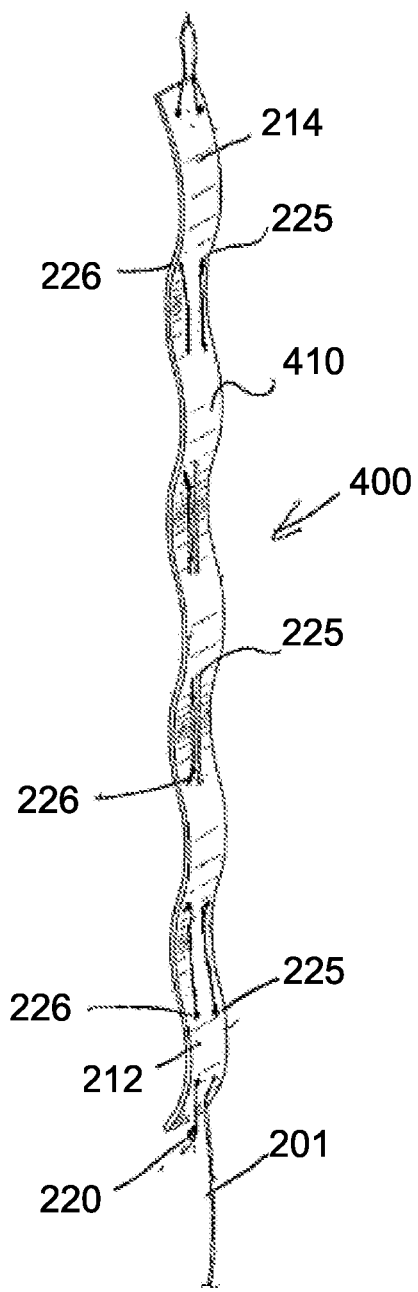
FIG. 9 is a perspective view of an anchor in accordance with some embodiments of the present teachings.

FIG. 9 illustrates an exemplary elongate profile of an exemplary anchor 400 that includes an elongate anchor member 410. The openings 225 in the first set of openings form a curve with the openings 225 in the middle portion of the anchor member closest to the lateral center of the anchor member 410, and the openings 226 in the second set of openings form another curve with the openings 226 in the middle portion of the anchor member 410 closest to the lateral center of the anchor member 410, and the two curves have a lateral distance from each other and together form an "hour glass" shape.

FIGS. 10A and 10B illustrate an exemplary elongate profile of an exemplary anchor 500 that includes an elongate anchor member 510. All openings 225, 226 in both sets of the openings are aligned with each other forming a straight line parallel to the longitudinal axis of the anchor member 510. FIG. 10B is a side elevation view of the anchor member 510 showing the routing of the tensioning member 201 through the anchor member 510.

Figure 12A:
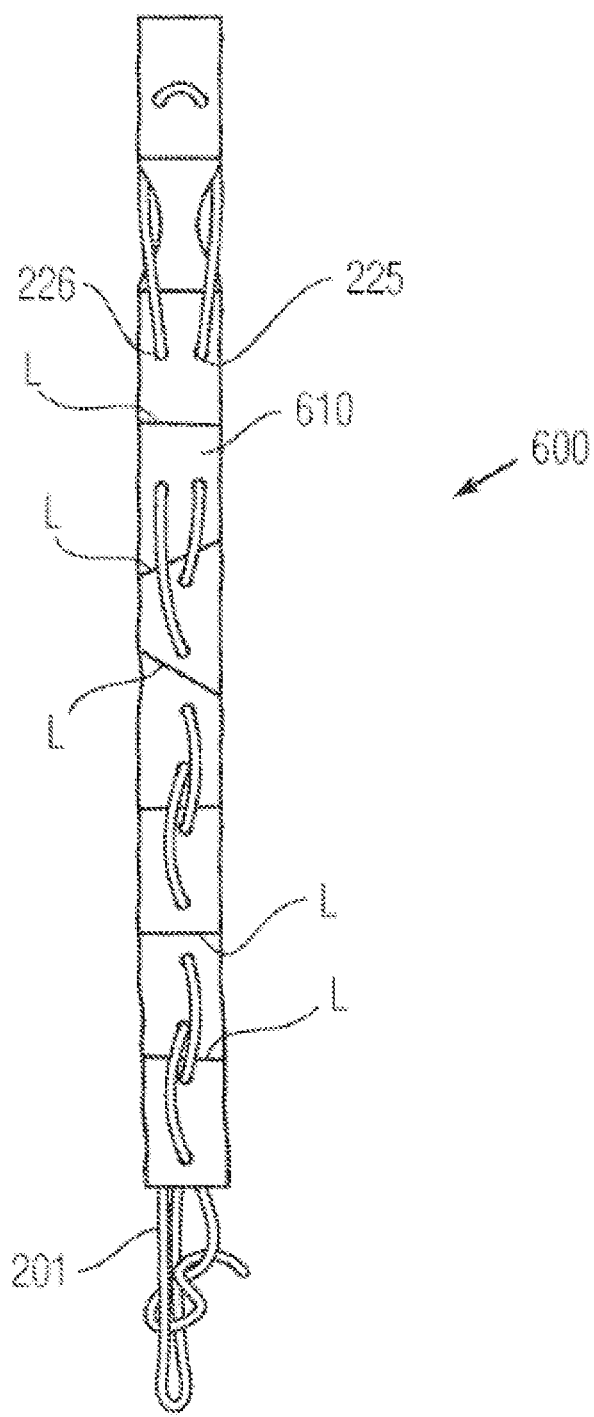
FIG. 12A is a perspective view of an anchor in accordance with some embodiments of the present teachings.

In various embodiments, at least one pre-set folding line is created between two pairs of the openings 225, 226, as illustrated in FIG. 12A. The pre-set folding line can be made by heat setting with or without a mold. One skilled in the art would understand that other methods can also be used to create pre-set folding lines without undue experimentations. In some embodiments, the pre-set folding lines allow the elongate anchor member to fold at pre-defined places. In certain embodiments, a pre-set folding line is created between every two pairs of the openings 225, 226, for example, as illustrated in FIGS. 8-10.

Figure 11:
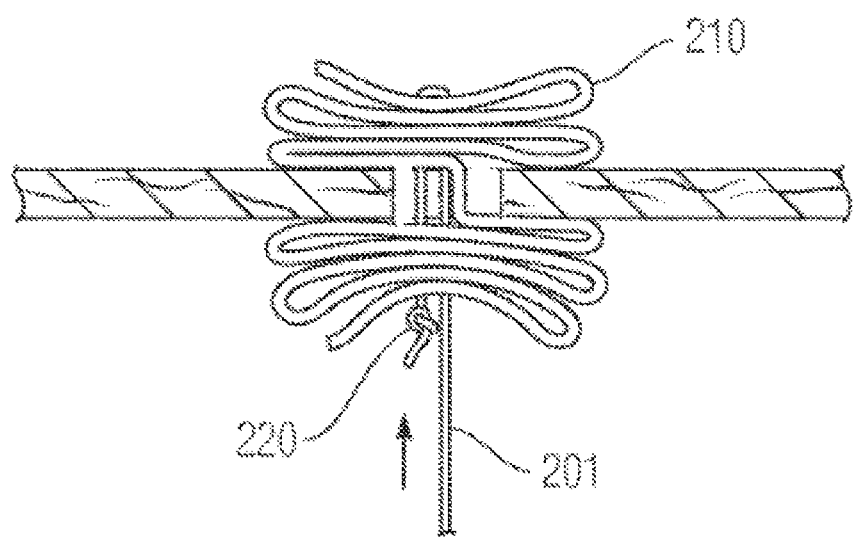
FIG. 11 is a perspective view of an exemplary anchor deployed across a paravalvular leakage in accordance with the present teachings.

According to various embodiments of the present teachings, the elongate anchor member (e.g., anchor member 210) shortens and creates folds as illustrated in FIG. 11. In some embodiments, the number of the folds in the anchor in its deployed profile ranges from 4 to 12. In various embodiments, the number of the folds is the same as the number of the openings in at least one set of the openings 225, 226. In other embodiments, the number of the folds has no particular relationship with the number of the openings in either set of the openings 225, 226. In various embodiments, the number of the folds is the same as the number of the pre-set folding lines plus one. In other embodiments, the number of the folds has no particular relationship with the number of the pre-set folding lines.

Figure 12B:
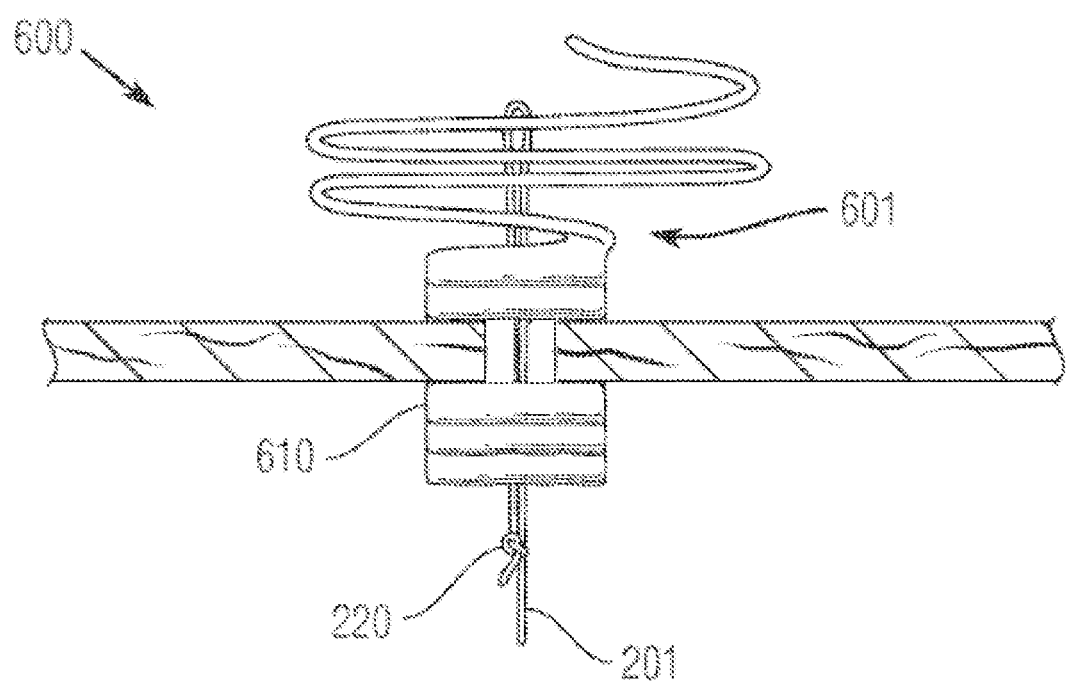
FIG. 12B is a cross-sectional view of an anchor deployed across a paravalvular leakage in accordance with some embodiments of the present teachings.
Figure 12C:
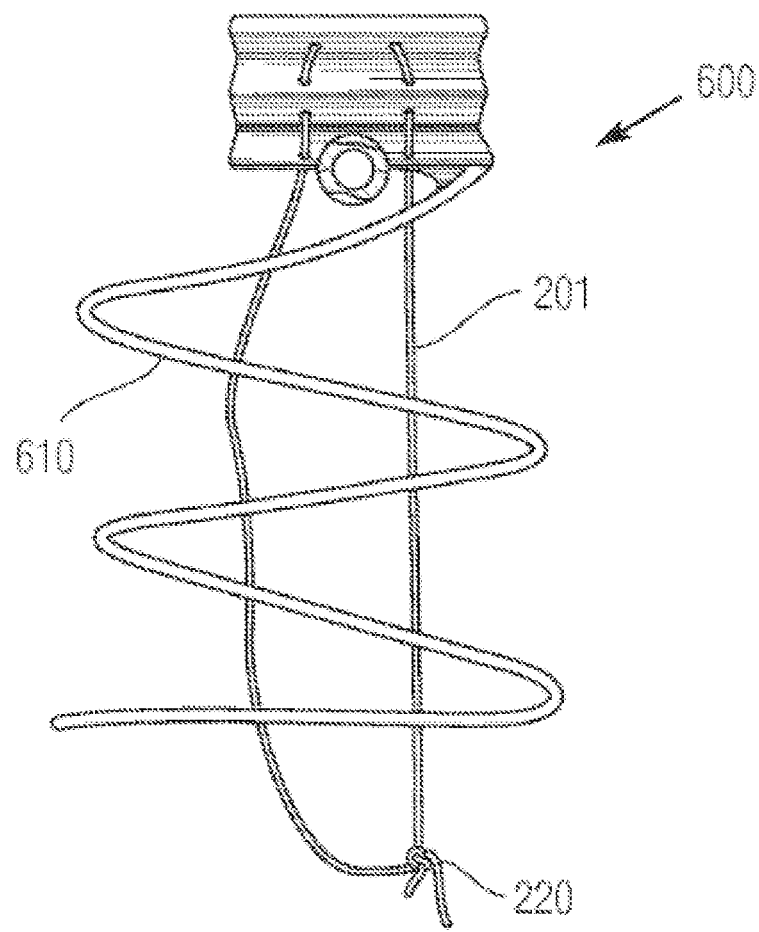
FIG. 12C is a side elevation view of the anchor of FIGS. 12A-12B.
Figure 12D:
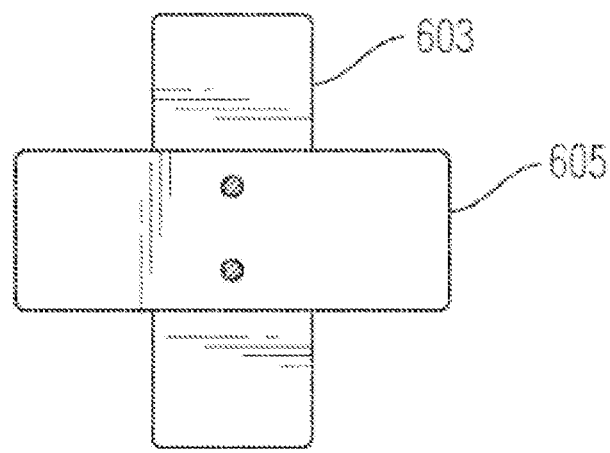
FIG. 12D is top plan view of the anchor of FIGS. 12A-12B.

FIGS. 12A-D illustrate an exemplary embodiment of the present teachings. Specifically, FIGS. 12A and 12D illustrate an exemplary elongate profile and an exemplary deployed profile, respectively, of an anchor 600 of the present teachings. The anchor 600 includes an elongate anchor member 610. As shown in FIG. 12A, the elongate anchor member 610 has two sets of openings 225, 226 through which the tensioning member 201 weaves. The tensioning member 201 weaves through the first set of openings 225 as it extends from the proximal end to the distal end of the anchor member 610 and weaves through the second set of openings 226 as it returns from the distal end to the proximal end of the anchor member 610.

In various embodiments of the present teachings, at least one opening in the first set of openings corresponds with another opening in the second set of openings and together they form a pair of openings on the anchor member. As shown in FIG. 12A, there are 5 pairs of openings 225, 226 in the distal portion of the anchor member, and 3 pairs of openings 225, 226 in the proximal portion of the anchor member 510. As shown in FIG. 12A, each pair of the openings 225, 226 in the distal end section of the distal portion of the anchor member form an imaginary line and the imaginary lines from the opening pairs 225, 226 in the distal portion of the anchor member 610 are parallel to one another and perpendicular to the longitudinal axis of the anchor member 610, and at the lateral center of the anchor member 610; all openings 225, 226 in the proximal end section of the distal portion of the anchor member 610 align with one another and form an imaginary straight line that is parallel to the longitudinal axis of the entire distal portion of the anchor member 610, and at the lateral center of the entire distal portion of the anchor member 610. Thus, in the proximal portion of the anchor member 610, all openings 225, 226 from both set of openings align with one another and form an imaginary straight line that is parallel to the longitudinal axis of the anchor member 610 and at the lateral center of the anchor member 610. One skilled in the art should understand that the amount of pairs of opening in distal and/or proximal portions of the anchor member 610 can be of any number other than what has been described here.

FIG. 12A further illustrates exemplary pre-set folding lines in an elongate anchor member of the present teachings. As shown in FIG. 12A, the folding lines (indicated in the drawings as "L") in the proximal portions and the distal end portion of the distal portion of the anchor member 610 are parallel to one another and perpendicular to the longitudinal axis of the anchor member 610. The pre-set folding lines L between the distal end section and proximal end section of the distal portion of the anchor member 610 are angled to the other pre-set folding lines L. Although specific pre-set folding patterns is shown in FIG. 12A, one with ordinary skill in the art would understand that other patterns, numbers can be incorporated to form pre-set folding lines L. For example, the both distal and proximal portions of the anchor member 610 are parallel to one another and perpendicular to the longitudinal axis of the anchor member 610, and only a middle portion 615 between the distal and proximal portions of the anchor member 610 are angled, so as to forming a transitional section across the paravalvular leakage upon deployment. Therefore what is shown in FIG. 12A should not be considered as being limiting.

FIG. 12A further illustrates an exemplary narrow section in the distal end portion of the anchor member. This narrow section is the result of radiopaque marker being crimped onto the anchor member. As described above, there are other ways of putting one or more radiopaque markers onto the anchor member. Thus, what is shown in this Figure should not limit the scope of the present teachings.

FIG. 12B illustrates an exemplary deployment profile of an embodiment of the present teachings across a paravalvular leakage site. There are 8 folds in the deployed anchor as shown in FIG. 12B, among which 5 are distal to the paravalvular leakage and 3 are proximal to the leakage. One skilled in the art would understand that the number of folds in each side of the paravalvular leakage should not be viewed as limiting. As shown in FIG. 12B, the folded panels at the proximal portion of the anchor member and at the proximal end section of the distal portion of the anchor member orientate in one direction, and the folded panels in the distal end portion of the anchor member orientate in another direction that is perpendicular to folded panels in the other direction. The transitional folds between the distal and proximal end section of the distal portion of the anchor member are located at the angled pre-set folding line. In this specific embodiment shown in FIG. 12B, the transitional folds are distal to the paravalvular leakage and are generally indicated with the reference character 601 (in other words, the change in folding direction is identified at 601). One skilled in the art should understand that the transitional folds can be proximal to the paravalvular leakage, or across the paravalvular leakage, and thus what has be illustrated here should not be viewed as limiting.

FIG. 12C is a view of the exemplary anchor shown in FIGS. 12A and B in its deployed configuration. The distal deployed anchor portion has a width "x" established by the width of the anchor and a length "y" determined by the distance between two pairs of the openings. The proximal deployed anchor portion has a width "y" established by the distance between the two pairs of the openings and a length "x" established by the width of the anchor. As shown in this view, the configuration in the exemplary embodiment shown in FIGS. 12A-D increases the overall width of the deployed anchor. This configuration prevents the tensioning member from cutting the panel and the paravalvular leakage and increases the retention force of the anchor against the leakage site.

In other words as shown in FIG. 12D, at least two adjacent anchor panels 603, 605 are disposed in a crisscrossed manner in that the longitudinal axes of the adjacent anchor panels 603, 605 are disposed perpendicular to one another as shown.

Other arrangements can be incorporated into the two sets of openings. For example, all the openings from both sets of openings in the distal portion of the anchor member can align with each other to form an imaginary straight line that is parallel to the longitudinal axis of the anchor member, and/or each pair of the openings in the proximal portion of the anchor member can form an imaginary line and all the imaginary lines so formed are parallel to one another and perpendicular to the longitudinal axis of the anchor member. One skilled in the art would understand that openings in either or both set of the openings can form any configuration so long as it serves the intended purpose.

Although the present teachings have been described with reference to preferred embodiments, persons ordinarily skilled in the art will recognize that changes can be made in form and detail without departing from the spirit and scope of the present disclosure.

What is claimed is:

1. A method of percutaneously treating a paravalvular leakage comprising the steps of:
   providing an anchor, wherein:
   the anchor comprises an elongate anchor member and a tensioning member, the elongate anchor member having a longitudinal axis,
   the elongate anchor member comprises a distal portion and a first set of openings along a length of the elongate anchor member, and the tensioning member passes through at least two of the first set of openings,
   the anchor has an elongate configuration and a shortened configuration,
   the elongate anchor member defines a first pre-set oblique folding line and a second pre-set oblique folding line, each of the first pre-set oblique folding line and the second pre-set oblique folding line being nonparallel and nonorthogonal to the longitudinal axis, and the second pre-set oblique folding line being nonparallel to the first pre-set folding line;
   positioning the anchor through a paravalvular leakage that comprises a gap defined between an artificial valve and a heart wall, wherein the anchor is positioned perpendicular to the artificial valve and heart wall;
   deploying the anchor wherein at least a part of the distal portion of the elongate anchor member is on one side of the paravalvular leakage; and
   plugging the paravalvular leakage by applying tension to the tensioning member so that the elongate anchor member transitions from the elongate configuration to the shortened configuration by folding about the first pre-set oblique folding line and the second pre-set oblique folding line.

2. The method of claim 1, wherein the elongate anchor member comprises a proximal portion.

3. The method of claim 2, wherein the elongate anchor member comprises a second set of openings.

4. The method of claim 2, wherein the tensioning member extends from the proximal portion to the distal portion of the elongate anchor member.

5. The method of claim 3, wherein the tensioning member extends from the distal portion to the proximal portion of the elongate anchor member.

6. The method of claim 5, wherein the tensioning member passes through at least two of the first set of openings.

7. The method of claim 5, wherein the tensioning member passes through at least two of the second set of openings.

8. The method of claim 2, further comprising the step of deploying the anchor wherein at least the part of the proximal portion of the elongate anchor member is on the other side of the paravalvular leakage.

9. The method of claim 2, further comprising the step of applying tension to the tensioning member so that at least the part of the proximal portion of the elongate anchor member transitions from the elongate configuration to the shortened configuration.

10. The method according to claim 2, wherein:
    the proximal portion defines a plurality of proximal pre-set folding lines that are parallel with each other, and the distal portion defines a plurality of distal pre-set folding lines that are parallel with each other, and
    plugging the paravalvular leakage by applying tension to the tensioning member comprises plugging the paravalvular leakage by applying tension to the tensioning member so that the elongate anchor member transitions from the elongate configuration to the shortened configuration by folding about the proximal pre-set folding lines and the distal pre-set folding lines.

11. The method according to claim 10, wherein:
    in the elongate configuration, the distal pre-set folding lines are parallel to the proximal pre-set folding lines, and
    plugging the paravalvular leakage by applying tension to the tensioning member comprises plugging the paravalvular leakage by applying tension to the tensioning member so that the elongate anchor member transitions from the elongate configuration to the shortened configuration by folding about the first pre-set folding line and the second pre-set folding line such that, in the shortened configuration, the distal pre-set folding lines are nonparallel to the proximal pre-set folding lines.

12. The method according to claim 11, wherein plugging the paravalvular leakage by applying tension to the tensioning member comprises plugging the paravalvular leakage by applying tension to the tensioning member so that the elongate anchor member transitions from the elongate configuration to the shortened configuration by folding about the first pre-set folding line and the second pre-set folding line such that, in the shortened configuration, the distal pre-set folding lines are orthogonal to the proximal pre-set folding lines.

13. The method of claim 1, further comprising the step of introducing a catheter approximately at the paravalvular leakage.

14. The method of claim 13 further comprising the step of withdrawing the catheter to deploy the anchor wherein at least a part of the distal portion of the elongate anchor member is on one side of the paravalvular leakage.

15. The method of claim 13, further comprising the step of withdrawing the catheter to deploy the anchor wherein at least a part of the proximal portion of the elongate anchor member is on the other side of the paravalvular leakage.

16. The method of claim 1 comprising the step of locating the paravalvular leakage.

17. The method of claim 1, wherein the elongate anchor member comprises a plurality of panels, wherein a least one of the plurality of panels is defined between the first pre-set oblique folding line and the second pre-set oblique folding line.

18. The method of claim 17, wherein at least two of the plurality of panels are at least one of substantially overlapping and partially overlapping in the shortened configuration.

19. The method of claim 17, wherein the applying of tension of the tensioning member causes at least two of the plurality of panels to fold about the first pre-set oblique folding line.

20. The method of claim 1, wherein the anchor comprises a second elongate anchor member proximally to the elongate anchor member.

21. The method of claim 20, further comprising the steps of:
    deploying the anchor, wherein at least a part of the second elongate anchor member is on the other side of the paravalvular leakage; and
    applying tension to the tensioning member so that at least a part of the second elongate anchor member transitions from the elongate configuration to the shortened configuration_.

22. The method of claim 21, further comprising introducing a catheter approximately at the paravalvular leakage; and
    withdrawing the catheter to deploy the anchor wherein at least a part of the elongate anchor member is on one side of the paravalvular leakage.

* * * * *